US011457994B2

(12) United States Patent
Jesurun et al.

(10) Patent No.: US 11,457,994 B2
(45) Date of Patent: Oct. 4, 2022

(54) SURGICAL LIGHT HEAD WITH BEAM SPREADING AND ADJUSTABLE POWER BALANCING

(71) Applicant: American Sterilizer Company, Mentor, OH (US)

(72) Inventors: David Jesurun, South Euclid, OH (US); Benjamin L. Yoder, Cleveland Heights, OH (US)

(73) Assignee: American Sterilizer Company, Mentor, OH (US)

( * ) Notice: Subject to any disclaimer, the term of this patent is extended or adjusted under 35 U.S.C. 154(b) by 74 days.

(21) Appl. No.: 17/153,974

(22) Filed: Jan. 21, 2021

(65) Prior Publication Data

US 2021/0236232 A1 Aug. 5, 2021

Related U.S. Application Data

(60) Provisional application No. 62/968,208, filed on Jan. 31, 2020.

(51) Int. Cl.
*A61B 90/30* (2016.01)
*F21V 5/00* (2018.01)
(Continued)

(52) U.S. Cl.
CPC .............. *A61B 90/30* (2016.02); *A61B 90/00* (2016.02); *F21V 5/008* (2013.01); *F21V 5/04* (2013.01);
(Continued)

(58) Field of Classification Search
CPC ... A61B 90/30; A61B 90/00; A61B 2090/308; A61B 90/35; A61B 2090/309;
(Continued)

(56) References Cited

U.S. PATENT DOCUMENTS 4,196,460 A 4/1980 Schreckendgust
6,857,772 B2 2/2005 Brukilacchio
(Continued)

FOREIGN PATENT DOCUMENTS

| DE | 102016105152 A1 | 9/2017 |
| EP | 2065634 B1 | 8/2017 |
| WO | 2019178779 A1 | 9/2019 |

OTHER PUBLICATIONS

International Search Report and Written Opinion for corresponding PCT International Application PCT/US2021/014268 dated May 10, 2021.

*Primary Examiner* — Bao Q Truong
(74) *Attorney, Agent, or Firm* — Renner, Otto, Boisselle & Sklar, LLP

(57) ABSTRACT

A light head for a medical device support system. The light head includes first and second zones of light sources, an optical system, and a control system. The first and second zones of light sources emit respective first and second beams of light that form an illumination pattern having a pattern size at a region of interest. The optical system adjusts a beam spread of the second beam of light to change the pattern size of the illumination pattern from a first pattern size to a second pattern size. The control system varies power to the first and second zones of light sources in response to adjustment of the beam spread of the second beam of light to maintain a substantially constant magnitude of illuminance at the region of interest as the pattern size is changed from the first pattern size to the second pattern size.

17 Claims, 9 Drawing Sheets

(51) Int. Cl.
*F21V 5/04* (2006.01)
*F21V 14/06* (2006.01)
*F21V 23/00* (2015.01)
*A61B 90/00* (2016.01)
*H05B 45/00* (2022.01)
*A61B 90/35* (2016.01)
*F21W 131/205* (2006.01)
*H05B 47/00* (2020.01)

(52) U.S. Cl.
CPC ............ *F21V 14/06* (2013.01); *F21V 23/003* (2013.01); *H05B 45/00* (2020.01); *A61B 90/35* (2016.02); *A61B 2090/308* (2016.02); *F21W 2131/205* (2013.01); *H05B 47/00* (2020.01)

(58) Field of Classification Search
CPC ........ H05B 45/00; H05B 47/00; H05B 47/11; H05B 47/105; H05B 47/10; H05B 45/10; F21V 5/008; F21V 5/04; F21V 14/06; F21V 23/003; F21V 9/00; F21V 14/00; F21V 23/00; F21W 2131/205
See application file for complete search history.

(56) References Cited

U.S. PATENT DOCUMENTS

| | | | |
|---|---|---|---|
| 6,964,490 B2 | 11/2005 | Scholz | |
| 7,513,645 B2 | 4/2009 | Marka et al. | |
| 7,922,347 B2 | 4/2011 | Kaletin et al. | |
| 8,134,309 B2 | 3/2012 | Marka et al. | |
| 8,201,966 B2 | 6/2012 | Hall et al. | |
| 9,119,668 B2 | 9/2015 | Marka et al. | |
| 9,289,269 B2 | 3/2016 | Valteau et al. | |
| 9,920,922 B2 | 3/2018 | Liang et al. | |
| 10,180,238 B2 | 1/2019 | Vu Thi et al. | |
| 10,271,398 B2 * | 4/2019 | Hollopeter | H05B 45/00 |
| 10,393,356 B2 | 8/2019 | Strolin | |
| 2003/0165055 A1 | 9/2003 | Scholz | |
| 2014/0066722 A1 | 3/2014 | Rudolf et al. | |
| 2016/0282630 A1 * | 9/2016 | Valteau | F21V 5/04 |
| 2016/0356458 A1 | 12/2016 | Hong et al. | |
| 2017/0296291 A1 * | 10/2017 | Barlund | G09F 19/18 |
| 2019/0324253 A1 | 10/2019 | Zapata et al. | |

* cited by examiner

SURGICAL LIGHT HEAD WITH BEAM SPREADING AND ADJUSTABLE POWER BALANCING

This application claims priority to U.S. Patent Application No. 62/968,208 filed Jan. 31, 2020. This prior application is incorporated herein by reference.

FIELD OF INVENTION

This application relates generally to a surgical light head for a medical device support system or carry system and a method of operating such a surgical light head, and more particularly to a surgical light head with beam spreading and adjustable power balancing and a method of operating such a light head.

BACKGROUND

Light heads for medical device support systems, suspension systems and/or other carry systems, are used in health treatment settings such as hospital examination rooms, clinics, surgery rooms and emergency rooms to illuminate a region interest such as a surgical treatment site or other medical site below the light heads. The light heads typically include a housing, one or more light sources mounted inside the housing, one or more lenses through which light emitted by the light sources is transmitted to the region of interest, and a handle mounted to the housing to enable a healthcare professional to adjust the position of the light head according to the needs of a specific medical procedure.

For light heads in some medical device support systems or carry systems, there remain various shortcomings, drawbacks, and disadvantages relative to certain applications.

For example, although there exist light heads for which a user may adjust an illumination pattern size of an emitted light beam at the region of interest, these light heads either fail to provide or inadequately provide adjustment to the light source(s) based on the illumination pattern size selected by the user. This can result in the illuminance at the region of interest either dimming considerably as the pattern size is increased or being excessively bright as the pattern size is decreased. In other words, as the pattern size is enlarged the same amount of light is spread over a larger or smaller area; since the total visible flux is constant, the illuminance decreases due to the larger area of the pattern size or increases due to the smaller area of the pattern size.

Some light heads provide means for varying power in different light source(s) according to conditions within the surgical field, for example to reduce shadow effects owing to blockage of light source(s). The downside here, however, is that the power variation does not maintain a uniform light distribution but rather only "fills in" shadows or other abnormalities caused by the conditions. The provision of illumination in highly concentrated areas, i.e. dark spots, leads to inconsistent illumination across the region of interest.

There also are light heads that are designed to form a desired beam at a specific distance by means of tilting a first set of light sources to produce a small illumination pattern at a region of interest and tilting a second set of light sources to produce an outer ring illumination pattern at the region of interest, the result being a large illumination pattern at the region of interest. The light head is able to adjust power to the different sets of light sources but, due to the different sets of light sources being directed to different portions of the region of interest, the light beam produced by the light head is inconsistent in size, shape, and uniformity, especially as the distance is varied from the light head to the region of interest. A further disadvantage of such a light head is that the light sources that are not used in producing the small pattern, i.e. the second set of light sources that form the outer ring, are essentially underutilized which is an inefficient use of space of the light head and inefficient use of the expensive components that make up the light sources.

Accordingly, there remains a need for further contributions in this area of technology.

SUMMARY OF INVENTION

According to one aspect of the invention, a light head for a medical device support system includes a first zone of light sources and a second zone of light sources, an optical system, and a control system. The first zone of light sources emits a first beam of light and the second zone of light sources emit a second beam of light, and the first and second beams of light form an illumination pattern having a pattern size at a region of interest. The optical system is arranged in a path of the second beam of light to adjust a beam spread of the second beam of light to change the pattern size of the illumination pattern at the region of interest from a first pattern size to a second pattern size. The control system is configured to vary power to the first and second zones of light sources in response to adjustment of the beam spread of the second beam of light by the optical system to maintain a substantially constant magnitude of illuminance at the region of interest as the pattern size of the illumination pattern at the region of interest is changed from the first pattern size to the second pattern size.

Embodiments of the invention may include one or more of the following additional features separately or in combination.

The control system may be configured to vary power to the first and second zones of light sources in response to adjustment of the beam spread of the second beam of light by the optical system to maintain a substantially constant magnitude of illuminance at a center of the region of interest as the pattern size of the illumination pattern at the region of interest is changed from the first pattern size to the second pattern size.

The control system may be configured to increase power to the second zone of light sources and decrease power to the first zone of light sources in response to the second pattern size being adjusted to be relatively larger than the first pattern size.

The light head may further include a handle mounted for rotational movement relative to a housing of the light head and coupled to the optical system, wherein rotation of the handle adjusts the optical system to adjust the beam spread of the second beam.

The optical system may include first and second wave lenses and rotation of the handle may move the first and second wave lenses relative to one another to adjust the beam spread of the second beam.

The control system may be configured to detect rotation of the handle and vary the power to the first and second zones of light sources based on the detected rotation.

The illumination pattern may include a first illuminance at the first pattern size and a second illuminance at the second pattern size, where the second illuminance is no more or no less than 15 percent different (+/−15 percent) from the first illuminance.

The illumination pattern may include a first illuminance at the first pattern size and a second illuminance at the second pattern size, where the second illuminance is no more or no less than 10 percent different (+/−10 percent) from the first illuminance.

The illumination pattern may include a first illuminance at the first pattern size and a second illuminance at the second pattern size, where the second illuminance is no more or no less than five percent different (+/−5 percent) from the first illuminance The control system may be configured to vary power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

The illumination pattern may have a diameter and a center, a d50/d10 ratio may be defined as a ratio of the diameter at which the illuminance reaches 50 percent (50%) of the illuminance value at the center of the illumination pattern, referred to as d50, over the diameter at which the illuminance reaches 10 percent (10%) of the illuminance value at the center of the illumination pattern, referred to as d10, and the substantially uniform illuminance across the illumination pattern may include the d50/d10 ratio being greater than 0.5.

The substantially uniform illuminance across the illumination pattern may include the d50/d10 ratio being greater than 0.6.

According to another aspect of the invention, a light head for a medical device support system includes a first zone of light sources and a second zone of light source, an optical system, and a control system. The first zone of light sources emit a first beam of light and the second zone of light sources emits a second beam of light. The first and second beams of light form an illumination pattern having a pattern size at a region of interest. The optical system is arranged in a path of the second beam of light to adjust a beam spread of the second beam of light to change the pattern size of the illumination pattern at the region of interest from a first pattern size to a second pattern size. The control system is configured to vary power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

According to another aspect of the invention, a method of operating a light head of a medical device support system includes emitting first and second beams of light by respective first and second zones of light sources, wherein the first and second beams of light form an illumination pattern having a pattern size at a region of interest; adjusting a beam spread of the second beam of light by an optical system in the path of the second beam of light to change the pattern size of the illumination pattern at the region of interest from a first pattern size to a second pattern size; and, varying power to the first and second zones of light sources in response to adjustment of the beam spread of the second beam of light by the optical system to maintain a substantially constant magnitude of illuminance at the region of interest as the pattern size of the illumination pattern at the region of interest is changed from the first pattern size to the second pattern size.

Embodiments of the invention may include one or more of the following additional features separately or in combination.

Varying power may include varying power to the first and second zones of light sources in response to adjustment of the beam spread of the second beam of light by the optical system to maintain a substantially constant magnitude of illuminance at a center of the region of interest as the pattern size of the illumination pattern at the region of interest is changed from the first pattern size to the second pattern size.

The method may further include varying power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

According to another aspect of the invention, a method of operating a light head of a medical device support system includes emitting first and second beams of light by respective first and second zones of light sources, wherein the first and second beams of light form an illumination pattern having a pattern size at a region of interest; adjusting a beam spread of the second beam of light by an optical system in the path of the second beam of light to change the pattern size of the illumination pattern at the region of interest from a first pattern size to a second pattern size; and, varying power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
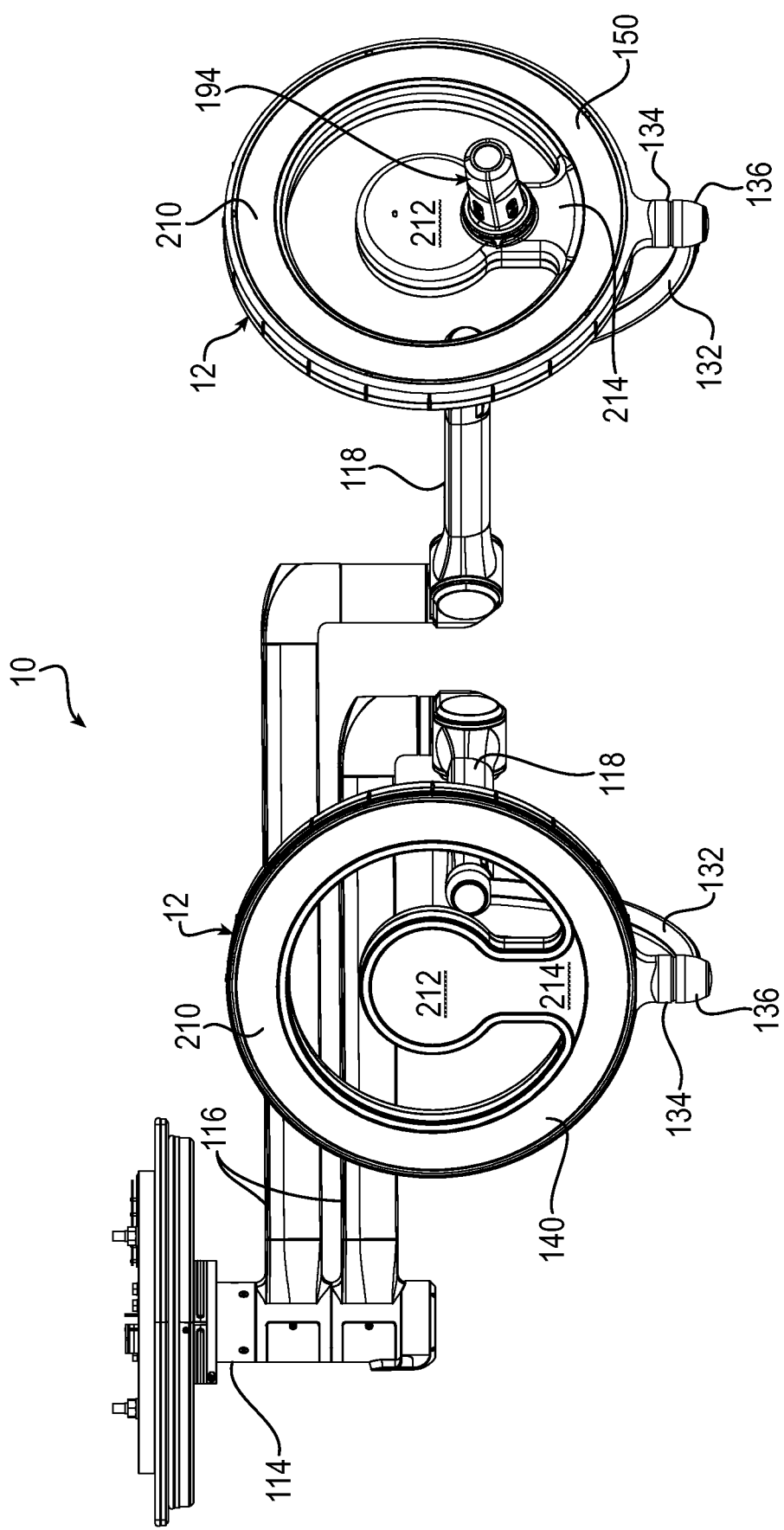
FIG. 1 is a side elevation view of an overall configuration of a medical device support system in accordance with an embodiment of the invention, showing a top of a left positioned light head and a bottom a right positioned light head.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

FIGS. 1-7 show a medical device support system 10 including two light heads 12 in accordance with an embodiment of the invention. Each light head 12 includes a first zone 14 of light sources 18 that emits a first beam of light 22 and a second zone 34 of light sources 38 that emits a second beam of light 42. The first beam of light 22 and the second beam of light 42 form an illumination pattern 52 having a pattern size at a region of interest 56. The region of interest 56 may be a surgical site or other medical site below the light heads 12. The light head 12 includes an optical system 60 that is provided in the paths of the first and second beams of light 22, 42. The optical system 60 is configured to adjust a beam spread of the second beam of light 42 to change the pattern size of the illumination pattern 52 at the region of interest 56 from a first pattern size 74 shown for example in FIG. 2 to a second pattern size 84 shown for example in FIG. 3. As will be described in greater detail below, a control system 90 is configured to vary power to the first zone 14 of light sources 18 and the second zone 34 of light sources 38 in response to adjustment of the beam spread of the second beam of light 42 by the optical system 60 to maintain a substantially constant magnitude of illuminance at the region of interest 56 as the pattern size of the illumination pattern 52 at the region of interest 56 is changed from the first pattern size 74 to the second pattern size 84.

Turning initially then to FIG. 1, the medical device support system 10 includes a central shaft or support column 114 that is suspended from the ceiling, and two generally horizontal extension arms 116 mounted to the shaft 114 for rotational movement about the shaft 114. The central shaft 114 could be mounted to a wall or stand rather than the ceiling. Two load balancing arms 118 are pivotably mounted to the distal ends of the respective extension arms 116. The distal ends of the load balancing arms 118 are configured with yoke assemblies 132 which, in turn, support the respective light heads 12 for multi-axis movement relative to the load balancing arms 118. Each light head 12 includes a bushing or other coupling member 134 that rotatably connects the light head 12 to the distal end of an arm 136 of a respective yoke assembly 132, as shown. The load balancing arms 118 and yoke assemblies 132 enable positioning of the light heads 12 to a proper orientation relative to for example the region of interest 56 and healthcare professionals in the operating room.

Figure 3:
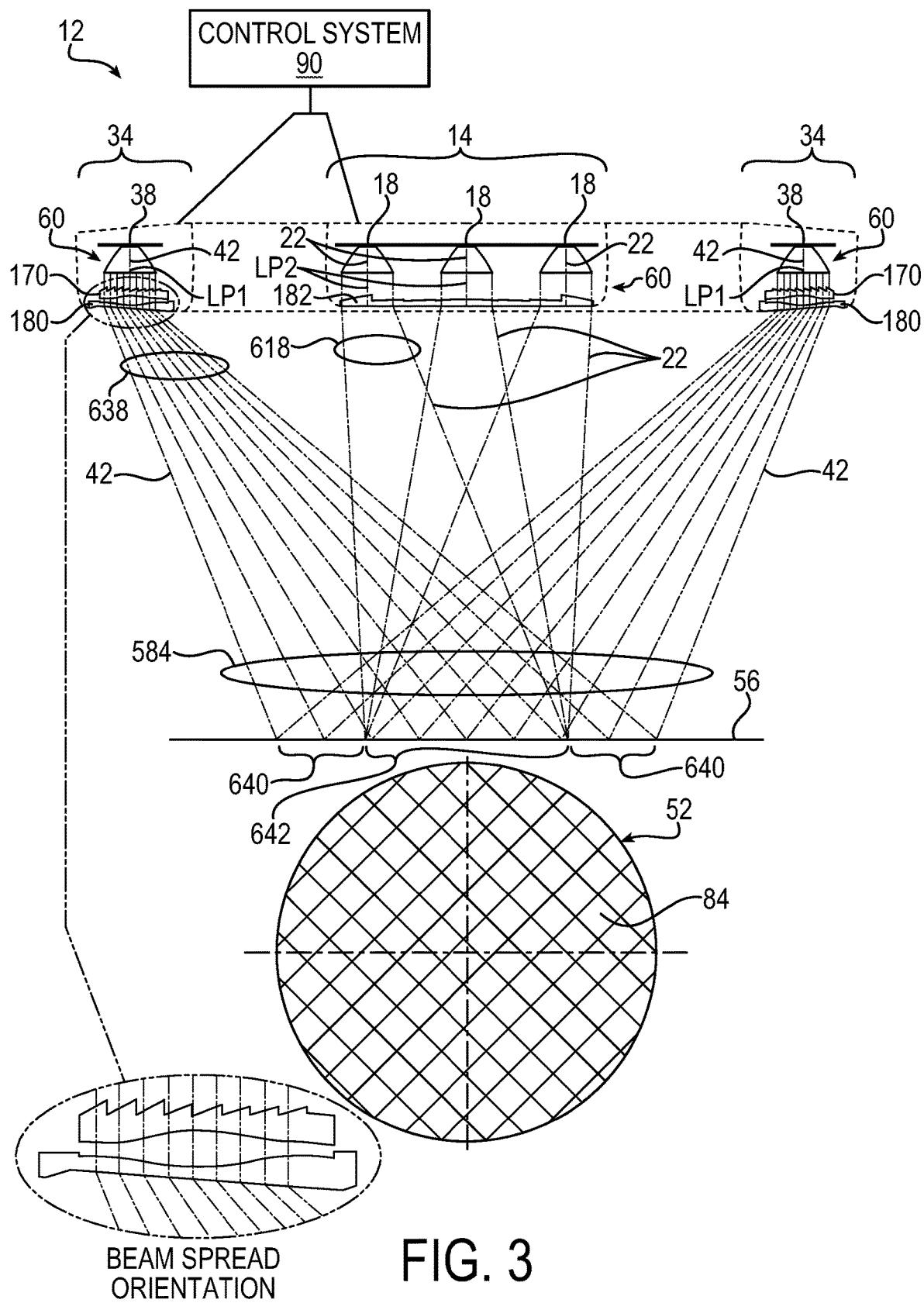
FIG. 3 is a cross section view of a relatively larger beam of light, and also shows at a lower portion thereof a top-down view of a relatively larger composite beam of light indicating surface density of radiant flux as a cross hatch pattern.
Figure 4:
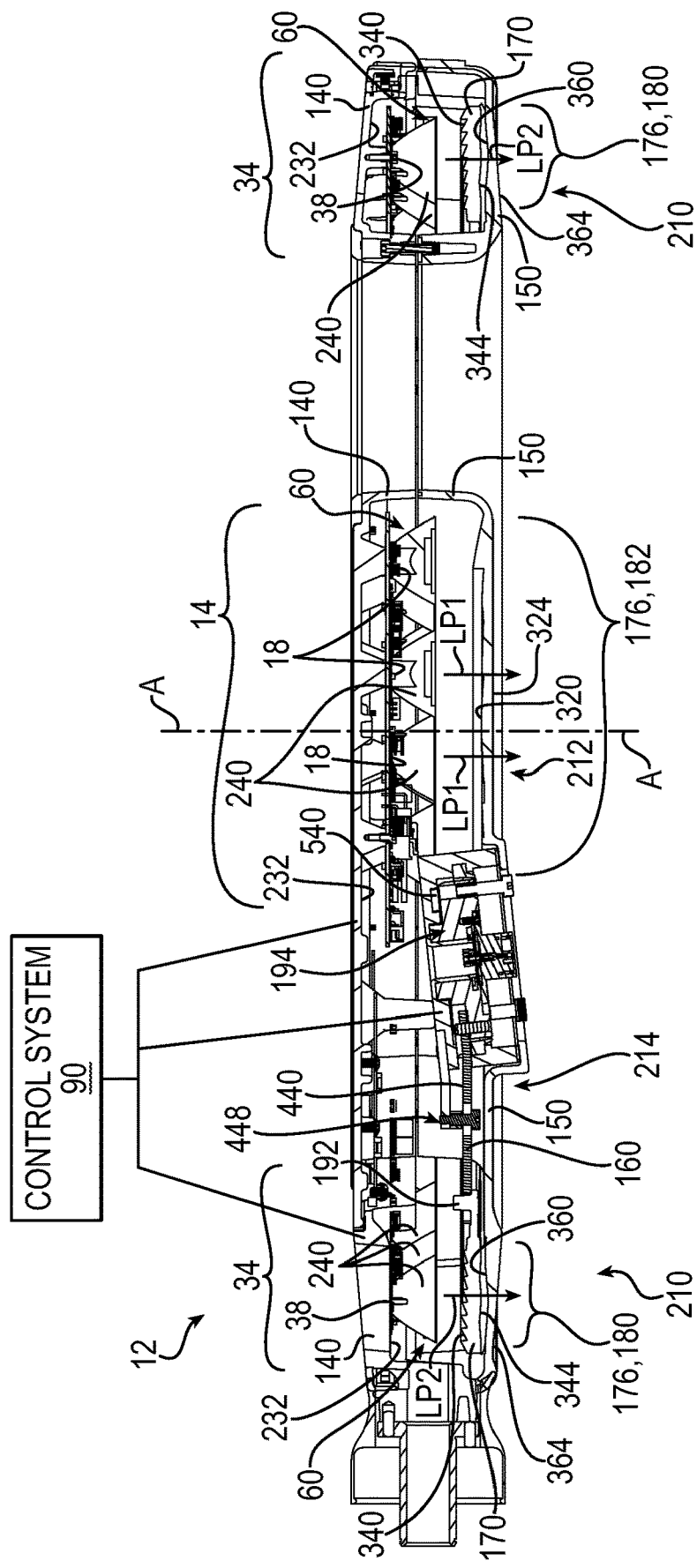
FIG. 4 is a side cross section view of a light head in accordance with an embodiment of the invention, showing a housing base, a housing cover, and internal components of the light head.
Figure 5:
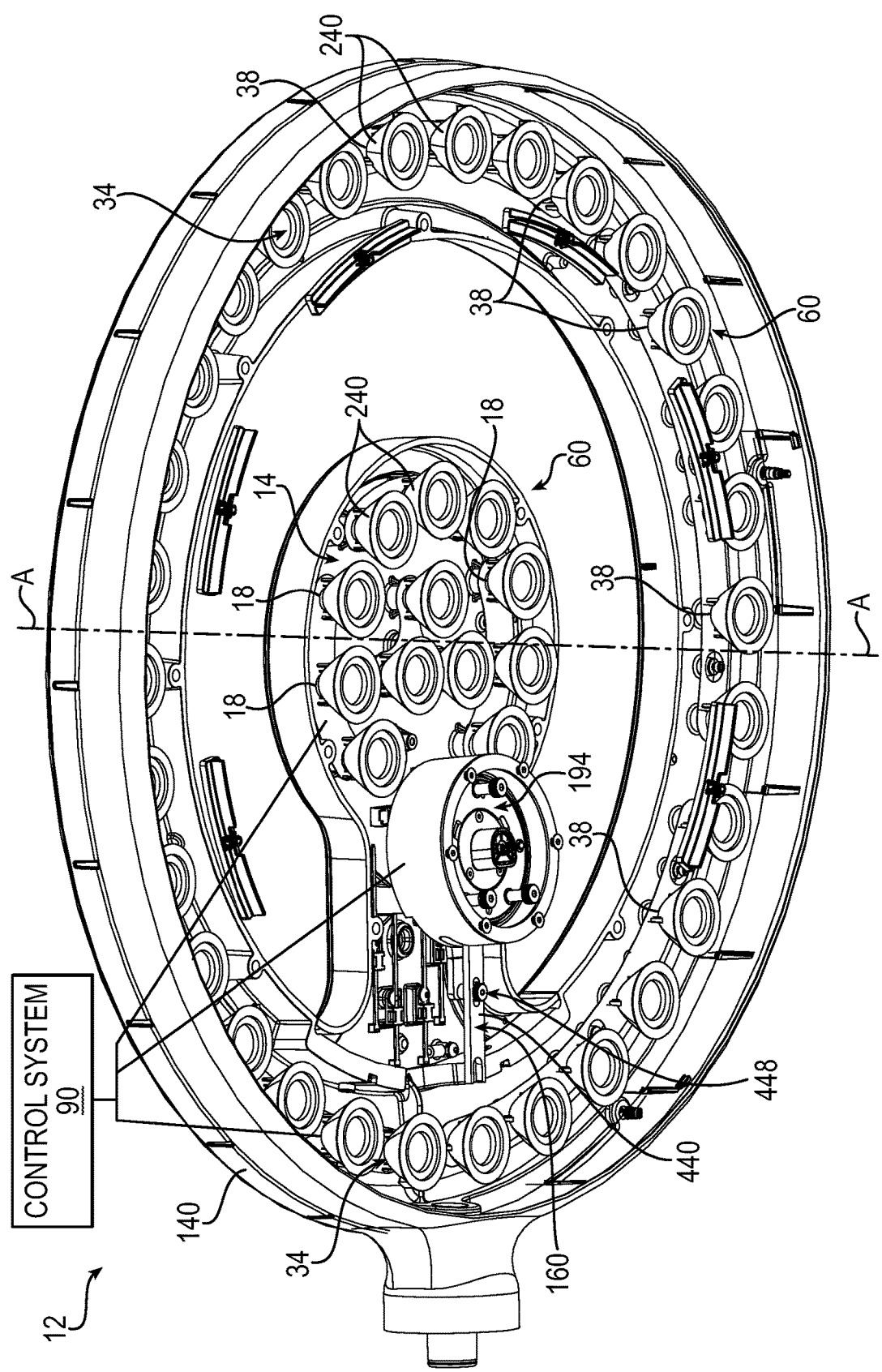
FIG. 5 is a bottom perspective view of the light head with a housing cover, handle and an annular shape lens omitted to show internal components of the light head.
Figure 6:
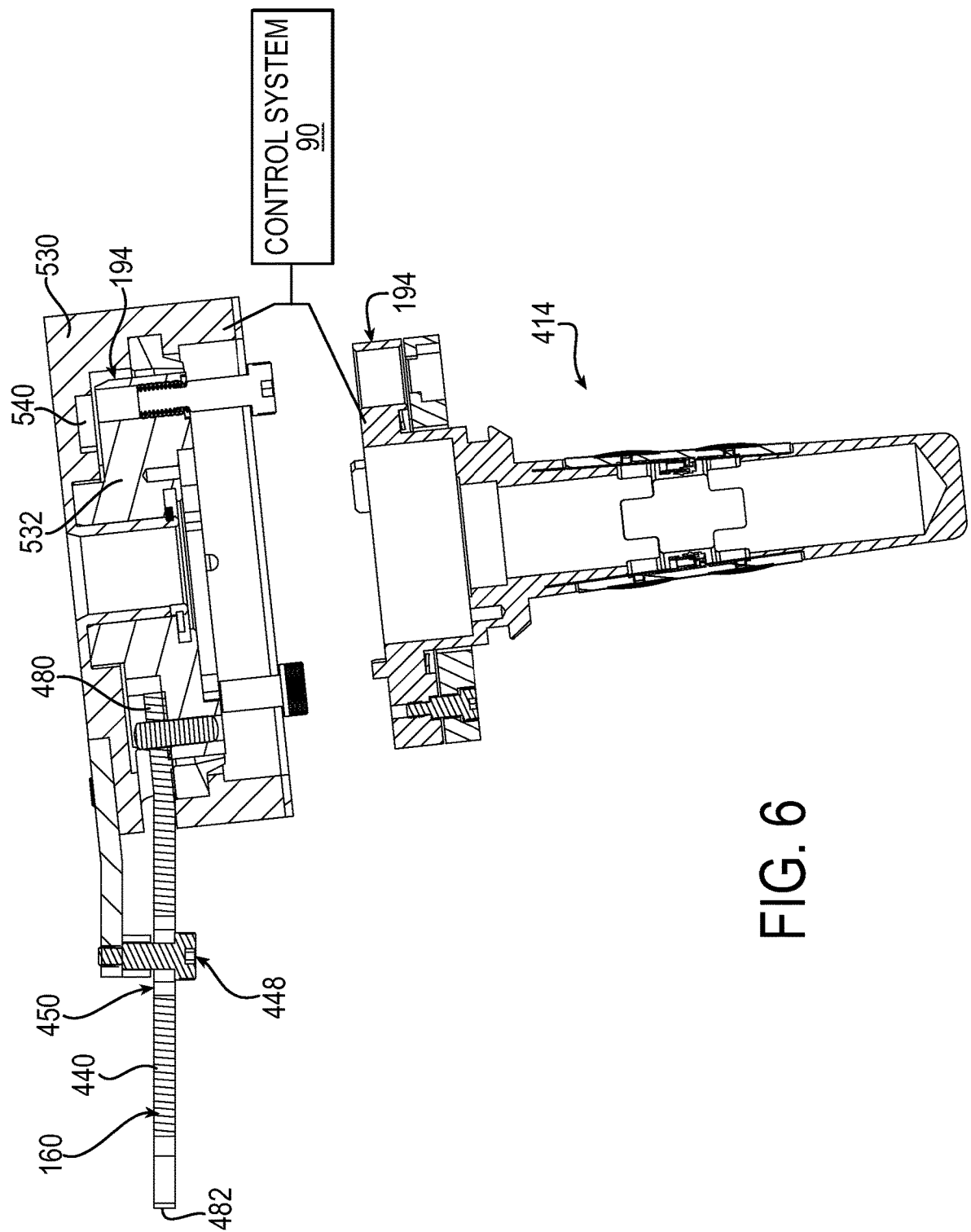
FIG. 6 is a side cross section view of a lever, hub, and a handle, showing the handle disconnected from the hub.

Referring to FIGS. 4-6, each light head 12 of the system 10 includes a housing base 140, the first and second zones 14, 34 of light sources 18, 38, the optical system 60, a housing cover 150, and a motion transfer member 160 which may include a lever, gear arrangement, or articulating assembly. The housing base 140 and the housing cover 150 together define an overall form and structure of the light head 12. The optical system 60 includes an annular shape lens 170 and a housing lens 176 made up of an annular shape outer housing lens 180 and an inner round housing lens 182. The annular shape lens 170 and the annular shape outer housing lens 180 are in a light emitting path LP2 of the second zone 34 of light sources 38 that emit the second beam of light 42 shown in FIGS. 1 and 3. The inner round housing lens 182 is in a light emitting path LP1 of the first zone 14 of light sources 18 that emit the first beam of light 22 shown in FIGS. 2 and 3. With reference to FIG. 4, the motion transfer member 160 is configured to movably interact with a boss 192 of the annular shape lens 170 to rotate the annular shape lens 170 about a rotation axis A-A and within a cavity of the housing cover 150. The motion transfer member 160 may be movably coupled to a driving source 194, such as a handle, of the light head 12 such that motion from the driving source 194 translates into rotation of the annular shape lens 170 about the rotation axis A-A.

As shown in FIGS. 4 and 5, each light head 12 includes an annular shape outer portion 210, an inner round portion 212, and a radially protruding arm 214 that connects the annular shape outer portion 210 to the inner round portion 212. In the illustrative embodiment, the radially protruding arm 214 arranges the annular shape outer portion 210 and the inner round portion 212 in concentric relation to one another, and in concentric relation to the rotation axis A-A of the annular shape lens 170. The radially protruding arm 214 also houses the motion transfer member 160 and one or more components of the driving source 194 for driving the motion transfer member 160. As will be described in greater detail below, the control system 90 is configured to control the light sources 18, 38 of the annular shape outer portion 210 and the inner round portion 212 to emit light to the region of interest 56 below the light heads 12. Also, in this regard, the first zone 14 of light sources 18 may be referred to as an inner zone 14 of light sources 18, and second zone 34 of light sources 38 may be referred to as an outer zone 34 of light sources 38. It will be appreciated that the annular shape outer portion 210 and the inner round portion 212, and/or the inner and outer zones 14, 34, need not be in concentric relation to one another and instead can be arranged by the protruding arm in eccentric relation to one another.

An inside surface 232 of the housing base 140 supports the first and second zones 14, 34 of light sources 18, 38, which may be for example light emitting diodes (LEDs). In the illustrative embodiment, the optical system 60 may also include a plurality of collimators 240 mounted to the inside surface 232 of the housing base 140 and in the light emitting paths LP1, LP2 of the respective first and second zones 14, 34 of light sources 18, 38. The collimators 240 collect and direct, and/or collimate, the light into narrow beams. In one form, the collimators 240 may comprise total internal reflection (TIR) lenses. Referring to FIG. 5, the annular shape outer portion of the housing base 140 includes the second zone 34 of light sources 38 and the inner round portion of the housing base 140 includes the first zone 14 of light sources 18. In the illustrative embodiment annular shape outer portion of the housing base 140 has 30 light sources 38 and collimators 240 evenly spaced 12 degrees apart, while the inner round portion of the housing base 140 has 12 light sources 18 and collimators 240 distributed in an outer ring of nine and a triangle of three within the outer ring.

FIG. 4 shows an axial arrangement of the light sources 18, 38, the collimators 240, the annular shape lens 170, and the housing lens 176, where axial refers to the direction of emission of light from the light heads 12, or downward in FIG. 4. The annular shape outer housing lens 180 and the inner round housing lens 182 are in the light emitting paths LP1, LP2 of the first and second zones 14, 34 of light sources 18, 38. The annular shape lens 170 is in the light emitting paths LP2 of the second zone 34 of light sources 38, positioned between the light sources 38 and the annular shape outer housing lens 180. The collimators 240 are also arranged in the light emitting paths LP1, LP2 of the first and second zones 14, 34 of light sources 18, 38, both in the annular shape outer portion 210 of the light head 12 positioned between the light sources 38 and the annular shape lens 170, and in the inner round portion 212 of the light head 12 positioned between the light sources 18 and inner round housing lens 182.

The annular shape lens 170 and the housing lens 176, and the collimators 240 if provided, may take on any form for spreading and/or bending the light emitted by the light sources 18, 38.

As shown for example in FIG. 4, the inner round housing lens 182 of the housing lens 176 has a top face 320 formed as a stepped surface, for example a plurality of Fresnel wedges, that bends individual portions of the light beams 22, and a bottom face 324 formed as a generally planar surface. The inner round housing lens 182 redirects, for example as by converging, the first beam of light 22 emitted by the first zone 14 of light sources 18 to the region of interest 56 to contribute light and thus illumination to the illumination pattern 52. The annular shape lens 170 has a top face 340 formed as a stepped surface, for example a plurality of Fresnel wedges, that bends individual portions of the light beams 38, and a bottom face 344 formed as a wavy or curved surface. The annular shape outer housing lens 180 of the housing lens 176, meanwhile, has a top face 360 formed as a wavy or curved surface and a bottom face 364 formed as a generally planar wedge-shaped surface, where a generally planar wedge-shaped surface refers to a generally planar surface that is not perpendicular to the direction of travel of the light beam emitted by the light sources 38 and collimators 240, for example. Rotation of the annular shape lens 170 and its wavy surface 344 relative to the annular shape outer housing lens 180 and its wavy surface 360 results in beam spreading (focusing) of the light beam, while simultaneously bending (aiming) of the light beam is achieved by the wedge-shaped surfaces 340, 364 of the annular shape lens 170 and the annular shape outer housing lens 180. The lenses 170, 180 redirect, for example as by converging, the second beam of light 42 emitted by the second zone 34 of light sources 38 to the region of interest 56 to contribute light and thus illumination to the illumination pattern 52. Further details of the top and bottom face features and characteristics that may be suitable for the annular shape lens 170 ("upper lens") and the housing lens 176 ("lower lens") can be found in U.S. patent application Ser. No. 16/278,301, published as U.S. Patent Application Publication No. 2019/0258068, and titled "Refractive Lens Array Assembly," which is incorporated by reference for all purposes as if fully set forth herein.

The motion transfer member 160 movably interacts with the boss 192 of the annular shape lens 170 to rotate the annular shape lens 170 about the rotation axis A-A. In the illustrative embodiment, the rotation axis A-A constitutes the central axis of the light head 12 including the central axis of the housing base 140 and the central axis of the housing cover 150. The rotation axis A-A of the annular shape lens 170 need not be the same as (coincide with) the central axis of the light head 12 itself, or the same as (coincide with) the central axis of the housing base 140 and/or the housing cover 150. Thus, for example, the rotation axis A-A of the annular shape lens 170 may be offset from the central axis of the housing base 140 and/or housing cover 150, particularly where the light head 12 includes additional or alternate type control elements, handles, connection brackets, contours, among others.

The driving source 194 and the motion transfer member 160 impart motion to the boss 192 of the annular shape lens 170. In the illustrative embodiment, the driving source 194 includes a handle 414. It will be appreciated that the light head 12 may incorporate alternate or additional types of driving sources. In one form, the driving source 194 may include a lever depending downward from the bottom of the light head 12 in a manner like that of the illustrative handle 414 and operatively coupled to the motion transfer member 160. In another form, the driving source 194 may be a slider that is slidable relative to a bottom surface of the light head 12 and operatively coupled to the motion transfer member 160. In still another form, the driving source 194 may include a rotary motor or linear motor operable for example by control elements in a surface the light head 12 and operatively coupled to the motion transfer member 160, or even a rotary motor or linear motor that is operable by a handle of the light head 12. In the illustrative embodiment, the motion transfer member 160 includes a lever 440. As was briefly noted above, the motion transfer member 160 may take on other forms. For example, the motion transfer member 160 may include a gear assembly whereby the driving source 194 imparts movement to a rotary gear or rack and the rotary gear or rack, in turn, impart motion to the annular shape lens 170. It will be appreciated that the motion transfer member 160 may be a series of levers and/or gears and/or gear trains, or any other type of motion transfer mechanism and/or articulating assembly capable of conveying motion from the driving source 194 to the annular shape lens 170.

The lever 440 is movable relative to a fulcrum 448 of the light head 12 at a pivot slider portion 450 of the lever 440. The lever 440 is configured to transfer motion from the driving source 194 at a first end 480 of the lever 440 into rotational motion of the annular shape lens 170 about the rotation axis A-A at a second end 482 of the lever 440 in response to movement of the lever 440 relative to the fulcrum 448. Referring to FIGS. 5 and 6, the handle 414 is rotatably mounted coaxially to a hub 530 of the light head 12. The first end 480 of the lever 440 is movably coupled to a bushing 532 of the handle 414 and the second end 482 of the lever 440 is movably coupled to the annular shape lens 170. The lever 440 is configured to transfer rotational motion of the handle 414 at the first end 480 of the lever 440 into rotational motion of the annular shape lens 170 at the second end 482 of the lever 440, which, as afore described, results in beam spreading (focusing) of the second beam of light 42, while simultaneously bending (aiming) of the second beam of light 42. Further details of a light head incorporating a rotating wave lens assembly can be found in U.S. Patent Application No. 62/968,196 filed Jan. 31, 2020, and titled "Light Head with Rotating Lens Assembly and Method of Operating Same," which is incorporated by reference for all purposes as if fully set forth herein.

As shown in FIGS. 4 and 6, the light head 12 also includes a sensor 540 configured to sense or detect movement of the driving source 194 that corresponds to the spreading of the second beam of light 42. In the illustrative embodiment, where the driving source 194 includes the handle 414, the sensor 540 senses or detects rotation of the handle 414 and generates an output signal for processing by the control system 90. The sensor 540 may comprise any type of sensor suitable for detecting or sensing movement in the driving source 194 where the movement is representative of the beam spreading of the second beam of light 42. It will be appreciated that beam spreading of the second beam of light 42 could be sensed by means other than sensing movement in the driving source 194. For example, a sensor may be provided that senses adjustment of the spread of the second beam of light 42 by, for example, sensing relative motion of the lenses 170, 180 that are in the light emitting paths LP2 of the light sources 38 that emit the second beam of light 42, or by sensing movement of the motion transfer member 160 such as the lever 440, or by sensing other conditions indicative of beam spreading.

Figure 2:
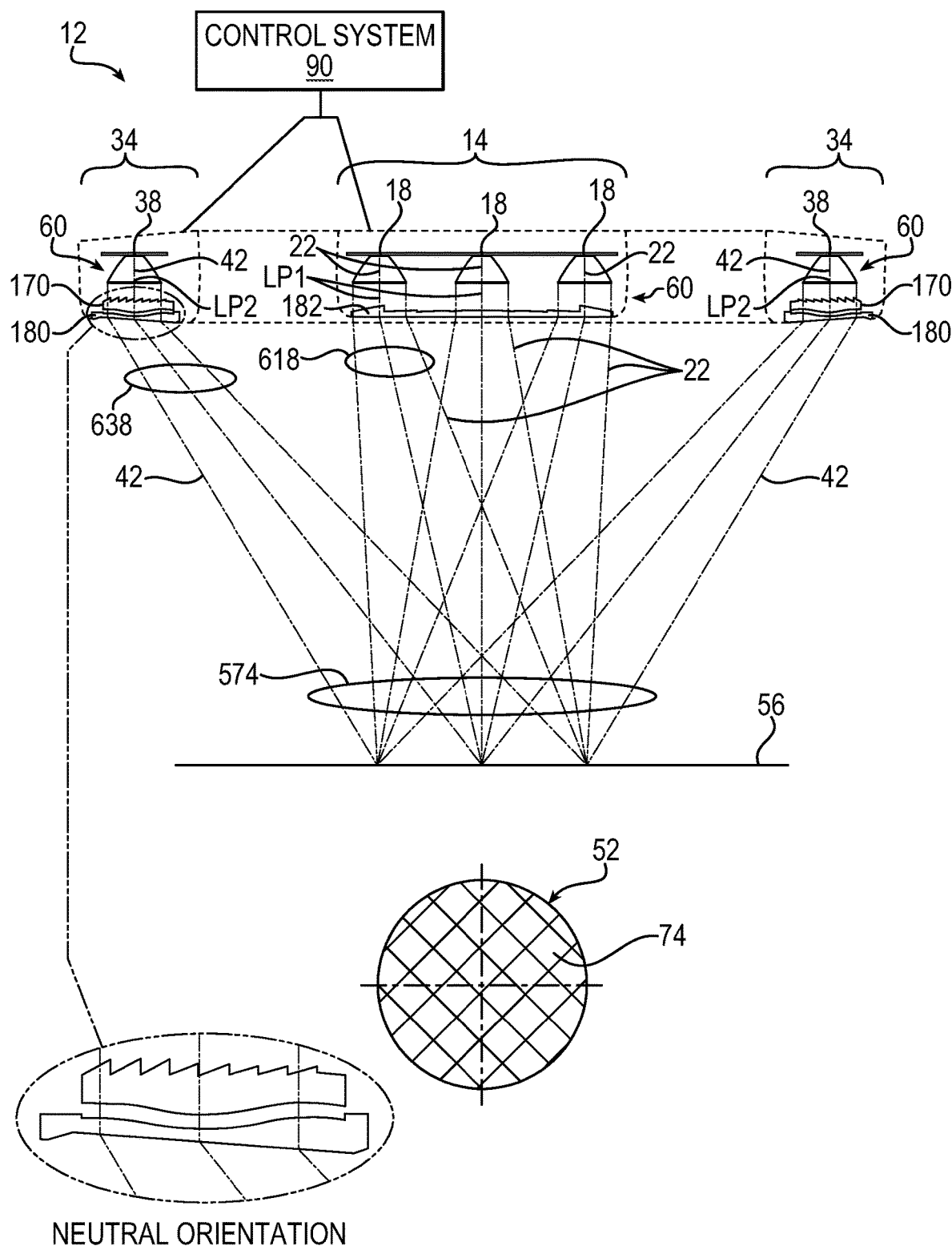
FIG. 2 is a cross section view of a relatively smaller beam of light, and also shows at a lower portion thereof a top-down view of a relatively smaller composite beam of light indicating surface density of radiant flux as a cross hatch pattern.
Figure 7:
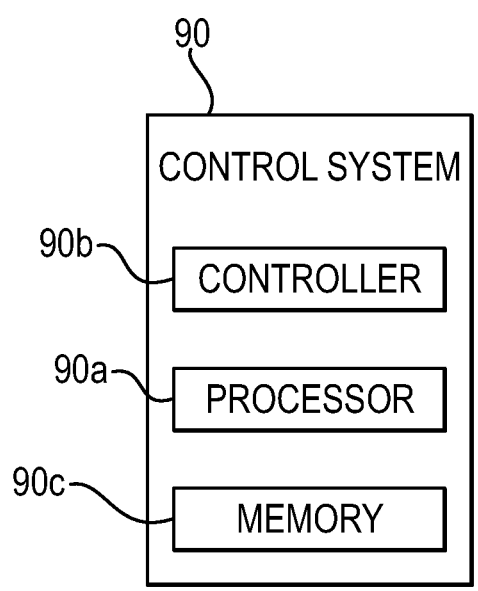
FIG. 7 is a block diagram of a control system for the medical device support system in accordance with an embodiment of the invention.

Referring to FIGS. 2, 3, and 7, the control system 90 is configured to vary power to the first zone 14 of light sources 18 and the second zone 34 of light sources 38 in response to adjustment of the beam spread of the second beam of light 42 by the optical system 60. Each light head 12 is communicatively coupled with the control system 90 which includes control elements integrated into the light head housing, handle, or support structure. FIG. 7 shows an exemplary control system 90. The control system 90 may include a main processor 90a including any suitable microprocessor, control processing unit (CPU), control circuitry, or the like. A controller 90b may be communicatively coupled between the processor 90a and components in the light head 12 for adjusting the components based on instructions received from the processor 90a. For example, the controller 90b may be configured to adjust a total visible flux of the light sources 18, 38, where the total visible flux refers to the radiant power of the light sources 18, 38 that is weighted by the sensitivity of the human eye. The common unit of the total visible flux is lumens. A memory 90c may also be provided as part of the control system 90. The memory 90c may contain stored data pertaining to operation of the light head 12 that is used by the processor 90a in providing instructions to the controller 90b. For example, the memory 90c may be configured to store data pertaining to total visible flux to be provided to the light sources 18, 38 as a function of adjustment of spread of the second beam of light 42 for example as sensed by the sensor 540, where the adjustment of the spread of the second beam of light 42 may be by, for example, relative motion of the lenses 170, 180 that are in the light emitting paths LP2 of the light sources 38 that emit the second beam of light 42, and where the relative motion of the lenses 170, 180 may be imparted by, for example, movement of the driving source 194 such as the handle 414, or movement of the motion transfer member 160 such as the lever 440, or other means. The memory 90c may include one or more look-up tables that store power values that correspond to, for example, beam spread, distance between the light head 12 and the region of interest 56, handle rotation, light head tilt angle, among others.

The term "control system" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

FIGS. 2 and 3 show respective side cross section views of the light head 12 emitting a relatively smaller beam of light 574 and a relatively larger beam of light 584. Each beam of light 574, 584 is formed by a composite of the first beam of light 22 emitted by the first zone 14 of light sources 18 and the second beam of light 42 emitted by the second zone 34 of light sources 38. In the illustrative embodiment, a single lens element 182 (for example Fresnel wedge lens, the inner round housing lens 182) is in the path of the first beam of light 22 of the first or inner zone 14 of light sources 18, and two-part lens elements 170, 180 (for example "wave lenses," the annular shape lens 170 and the annular shape outer housing lens 180) are in the second beam of light 42 of the second or outer zone 34 of light sources 38. FIG. 2 shows the wave lenses 170, 180 in their neutral orientation which generates a relatively smaller second beam of light 42 and relatively smaller pattern size 74. FIG. 3 shows the wave lenses 170, 180 in their beam spread orientation which generates the relatively larger second beam of light 42 and relatively larger pattern size 84. In the illustrative embodiment, the first beam of light 22 from the first zone 14 is not spread by the wave lenses 170, 180 but rather is bent or redirected by the single lens element 182. In the illustrative embodiment, each composite beam of light 574, 584 is round shape although other shapes are contemplated, as would occur for example when the light head 12 may be tilted relative to the region of interest 56.

The lower portions of FIGS. 2 and 3 show respective top-down views of the illumination pattern 52 generated by the composite beams of light 574, 584 at the region of interest 56. The FIG. 3 illumination pattern 52 has a pattern size 84 that is relatively larger than the pattern size 74 of the FIG. 2 illumination pattern 52 owing to the spreading of the second beam of light 42 by the optical system 60, more particularly by the relative movement between the annular shape lens 170 and the annular shape outer housing lens 180 of the optical system 60.

The cross hatch patterns (checkered patterns) shown in the lower portions of FIGS. 2 and 3 indicate a surface density of the radiant flux, also referred to herein as the magnitude of illumination, also referred to as illuminance, of the composite beams of light 574, 584 at for example the region of interest 56. The common unit of illuminance is the lux, also defined as one lumen per square meter. In FIGS. 2 and 3, the cross hatch patterns are identical, indicating that the magnitude of the illuminance at the region of interest 56 in FIG. 2 is substantially the same as the magnitude of the illuminance at the region of interest 56 in FIG. 3.

Also in FIGS. 2 and 3, the lines 618, 638 from the light head 12 to the region of interest 56 represent light rays with the amount of rays or lines per light source 18, 38 indicating the relative total visible flux 618, 638, or radiant power, emitted by the light sources 18, 38. Thus, in FIG. 2 the total visible flux 618, represented by three lines in FIG. 2, of the light sources 18 is the same as the total visible flux 638, also represented by three lines in FIG. 2, of the light sources 38. On the other hand, in FIG. 3, the total visible flux 618, represented by two lines in FIG. 3, of the light sources 18 is relatively less than the total visible flux 638, represented by nine lines in FIG. 3, of the light sources 38. It will be appreciated that FIGS. 2 and 3 are not to scale to allow better visualization and understanding of the invention.

Turning now to FIGS. 4-7 in conjunction with FIGS. 2 and 3, rotation of the handle 414 imparts motion to the lever 440 which, in turn, rotates the annular shape lens 170 relative to the annular shape outer housing lens 180 to spread the second beam of light 42, where FIG. 2 shows the relatively smaller pattern size 74 and FIG. 3 shows the relatively larger, i.e. spreaded, pattern size 84. As the pattern size of the illumination pattern 52 changes, either by increasing or decreasing pattern size, the control system 90 changes the total visible flux 618, 638 of the light sources 18, 38, for example by varying the power to the light sources 18, 38, to maintain the magnitude of the illuminance substantially constant, as indicated by the same cross hatch pattern in FIGS. 2 and 3.

Substantially constant magnitude illuminance refers to an illuminance of the illumination pattern 52 including a first illuminance (in units of lux) at the illumination pattern 52 having the first pattern size 74 (for example FIG. 2) and a second illuminance (in units of lux) at the illumination pattern 52 having the second pattern size 84 (for example FIG. 3), where the second illuminance is no more or no less than preferably 15 percent different (+/−15 percent) from the first illuminance, more preferably 10 percent different (+/−10 percent) from the first illuminance, and most preferably five percent different (+/−5 percent) from the first illuminance.

It will be appreciated that substantially constant magnitude illuminance may refer to the illuminance of the illumination pattern 52 at any portion of the illuminance pattern 52, for example, the center of the illumination pattern 52, a certain radial distance from the center of the illumination pattern 52, a periphery of the illumination pattern 52, or even a combination and/or an average of one or more of the foregoing. Thus, in one form, substantially constant magnitude illuminance may refer to an illuminance of the illumination pattern 52 including a first illuminance (in units of lux) at a center of the illumination pattern 52 having the first pattern size 74 (for example FIG. 2) and a second illuminance (in units of lux at) a center of the illumination pattern 52 having the second pattern size 84 (for example FIG. 3), where the second illuminance is no more or no less than preferably 15 percent different (+/−15 percent) from the first illuminance, more preferably 10 percent different (+/−10 percent) from the first illuminance, and most preferably five percent different (+/−5 percent) from the first illuminance.

In another form, substantially constant magnitude illuminance may refer to an illuminance of the illumination pattern 52 including a first illuminance (in units of lux) at a certain radial distance from the center of the illumination pattern 52 having the first pattern size 74 (for example FIG. 2) and a second illuminance (in units of lux) at a certain radial distance from the center of the illumination pattern 52 having the second pattern size 84 (for example FIG. 3), where the second illuminance is no more or no less than preferably 15 percent different (+/−15 percent) from the first illuminance, more preferably 10 percent different (+/−10 percent) from the first illuminance, and most preferably five percent different (+/−5 percent) from the first illuminance.

In another form, substantially constant magnitude illuminance may refer to an illuminance of the illumination pattern 52 including a first illuminance (in units of lux) at a center of the illumination pattern 52 having the first pattern size 74 (for example FIG. 2) and a second illumination (in units of lux) at a certain radial distance from the center of the illumination pattern 52 having the second pattern size 84 (for example FIG. 3), where the second illuminance is no more or no less than preferably 15 percent different (+/−15 percent) from the first illuminance, more preferably 10 percent different (+/−10 percent) from the first illuminance, and most preferably five percent different (+/−5 percent) from the first illuminance.

In yet another form, substantially constant magnitude illuminance may refer to an illuminance of the illumination pattern 52 including a first illuminance (in units of lux) that is an average of an illuminance at a center and an illuminance at a certain distance from center of the illumination pattern 52 having the first pattern size 74 (for example FIG. 2) and a second illuminance (in units of lux) that is an average of an illuminance at a center and an illuminance at a certain radial distance from center of the illumination pattern 52 having the second pattern size 84 (for example FIG. 3), where the second illuminance is no more or no less than preferably 15 percent different (+/−15 percent) from the first illuminance, more preferably 10 percent different (+/−10 percent) from the first illuminance, and most preferably five percent different (+/−5 percent) from the first illuminance.

One way to assess uniformity of illuminance across the illumination pattern 52 is by calculating the ratio of the diameter at which the illuminance reaches 50 percent (50%) of the maximum or central value (the illuminance at the center of the illumination pattern 52), referred to as d50, over the diameter at which the illuminance reaches 10% of the central value, referred to as d10. This ratio, referred to as d50/d10, is preferably greater than 0.5 and even more preferably greater than 0.6. Thus, for example, in the illustrative embodiment the diameter of the center portion 642 (where for example the illuminance is 50 percent of the illuminance value at the center of the illumination pattern 62) is greater than or equal to 50 percent (50%) of the diameter of the portion 640 (where the illuminance is 10% of the illuminance value at the center of the illumination pattern 52) yielding a d50/d10 of about 0.5. Further, for example, where in the illustrative embodiment the diameter of the center portion 642 (where for example the illuminance is 50 percent (50%) of the illuminance value at the center of the illumination pattern 62) is greater than or equal to 60% of the diameter of the portion 640 (where the illuminance is 10% of the illuminance value at the center of the illumination pattern 52) yielding a d50/d10 of about 0.6.

It will be appreciated that the natural tendency of the illuminance to decrease with increasing radial distance from the center of the illumination pattern 52 will also affect the illuminance across the illumination pattern 52. The control system 90 may be configured to process for example empirical data inputs indicative of how "smoothly" the decrease occurs and, based on such empirical data inputs, adjust the power to the first and second zones 14, 34 of light sources 18, 38. The control system 90 may be configured to adjust illuminance based one or both of empirical data inputs and the afore described d50/d10 ratio.

Thus, the rotation of the handle 414 mechanically moves the wave lenses 170, 180 relative to one another to adjust the spread of the beam of light 42 from the outer zone 34 of light sources 38, the control system 90 senses the rotation of the handle 414, for example as by receipt of the output signal from the sensor 540, and, based on this sensed handle rotation, the control system 90 adjusts the power to the inner and outer zones 14, 34 of light sources 18, 38 as needed to maintain a substantially constant illuminance in the illumination pattern 52 of the composite beam of light 574, 584, for example a substantially constant illuminance in the center of the illumination pattern 52 or a substantially constant illuminance at a certain radial distance from the center of the illumination pattern 52, as the pattern size of the illumination pattern 52 changes from the first pattern size 74 to the second pattern size 84.

The control system 90 is configured to change the total visible flux 618 and/or the total visible flux 638 based on an input, or inputs, representative of or indicative of a change in the beam spread of the second beam of light 42, or a change in the pattern size of the illumination pattern 52 at the region of interest 56 from, for example, the first pattern size 74 to the second pattern size 84, or the second pattern size 84 to the first pattern size 74. In an embodiment, the control system 90 may be configured to sense rotation of the handle 414 for example by the sensor 540 and, depending on the sensed rotation, change the total visible flux 618, 638 of the light sources 18, 38. For example, if clockwise rotation of the handle 414 results in spreading of the beam of light 42 from that which is shown in FIG. 2 to that which is shown in FIG. 3, then the control system 90 increases the total visible flux 638 of the light sources 38 (from three lines in FIG. 2 to nine lines in FIG. 3) while decreasing the total visible flux 618 of the light sources 18 (from three lines in FIG. 2 to two lines in FIG. 3). Conversely, if counterclockwise rotation of the handle 414 results in narrowing of the beam of light 42 from that which is shown in FIG. 3 to that which is shown in FIG. 2, then the control system 90 decreases the total visible flux 638 of the light sources 38 (from nine lines in FIG. 3 to three lines in FIG. 2) while increasing the total visible flux 618 of the light sources 18 (from two lines in FIG. 3 to three lines in FIG. 2).

It will be appreciated that the control system 90 may be configured to increase and/or decrease the total visible flux 618, 638 of the respective light sources 18, 38 according to any suitable input(s) and need not be limited to, for example, sensed rotation of the handle 414 or other driving source 194. For example, the control system 90 may be configured to increase and/or decrease the total visible flux 618, 638 of the respective light sources 18, 38 according to sensed movement of the annular shape lens 170, or movement of the annular shape lens 170 relative to the annular shape outer housing lens 180. In another form, the control system 90 may be configured to increase and/or decrease the total visible flux 618, 638 of the respective light sources 18, 38 according sensed movement of the lever 440 and, based on such sensed movement, change the total visible flux 618, 638 of the light sources 18, 38. In another form, the driving source 194 may be a rotary motor rather than the handle 414 and the control system 90 may be configured to increase and/or decrease the total visible flux 618, 638 of the respective light sources 18, 38 according sensed rotary motion of the motor and change the total visible flux 618, 638 based on such sensed rotary motion. In yet another form, the motion transfer member 160 may be a gear train rather than the lever 440 and the control system 90 may be configured to increase and/or decrease the total visible flux 618, 638 of the respective light sources 18, 38 according to a sensed particular movement in the gear train and change the total visible flux 618, 638 according to such particular gear movement.

In the illustrative embodiment, as the size of the illumination pattern 52 is changed from the relatively smaller pattern size 74 in FIG. 2 to the relatively larger pattern size 84 in FIG. 3, or vice versa, the control system 90 changes the total visible flux 618, 638 of the light sources 18, 38 to maintain the magnitude of the illuminance substantially constant. Referring to FIG. 2, the control system 90 controls the total visible flux 618 of the first zone 14 of light sources 18 (three rays or lines) to be about the same as the total visible flux 638 of the second zone 34 of light sources 38 (three rays or lines). Thus, in FIG. 2, the control system 90 controls the first or inner zone 14 of light sources 18 to produce the same total visible flux as the second or outer zone 34 of light sources 38, although with differing number of light sources 18, 38 (in the illustrative embodiment 12 light sources 18 in the inner zone 14 and 30 light sources 38 in the outer zone 34, see FIGS. 4 and 5), and the inner and outer zones 14, 34 produce the same illuminance since both zones 14, 34 also emit respective pattern sizes of the same size, pattern size 74. Referring to FIG. 3, the control system 90 controls the total visible flux 618 of the first zone 14 of light sources 18 (two rays or lines) to be relatively less than the total visible flux 638 of the second zone 34 of light sources 38 (nine rays or lines). Thus, in FIG. 3, the control system 90 controls the second or outer zone 34 of light sources 38 to produce more total visible flux 638 than in FIG. 2 but substantially the same illuminance as in FIG. 2 since the pattern size 84 in FIG. 3 is larger than the pattern size 74 in FIG. 2. Thus, for example, the illuminance at the center of the illumination pattern 52 in FIG. 3 will be no more or no less than preferably 15 percent different (+/−15 percent) from the illuminance at the center of the illumination pattern 52 in FIG. 2, more preferably 10 percent different (+/−10 percent) from the illuminance at the center of the illumination pattern 52 in FIG. 2, and most preferably five percent different (+/−5 percent) from the illuminance at the center of the illumination pattern 52 in FIG. 2.

The control system 90 may be configured to compensate for less illuminance or greater illuminance in the illumination pattern 52, or portions thereof, at the region of interest 56 by adjusting the total visible flux 618, 638 of, i.e. balancing the radiant power to, the respective first and second zones 14, 34 of light sources 18, 38. For example, in FIG. 2, the control system 90 may control the first or inner zone 14 of light sources 18 to produce for example half the illuminance at the relatively smaller pattern size 74 at the region of interest 56 and control the second or outer zone 34 of light sources 38 to likewise produce for example half the illuminance at the region of interest 56. For the relatively larger pattern size 84 of FIG. 3, the control system 90 may control the second or outer zone 34 of light sources 38 to produce substantially all the illuminance at the portion 640 surrounding the center portion 642 of the illumination pattern 52. It will be appreciated that with respect to the cross section view shown in FIGS. 2 and 3 there are more light sources 18, 38 than shown; that is, for the example light head 12 described herein the light head 12 is round with 12 light sources 18 in the inner zone 14 and 30 light sources 38 in the outer zone 34.

The control system 90 may be configured to power balance, or compensate, based on two different effects occurring at the region of interest 56. The first effect is that the spreading of the light emitted by the outer zone 34 of light sources 38 decreases the illuminance of the illumination pattern 52 at the region of interest 56. The control system 90 compensates for such decreased illuminance effect by increasing the total visible flux 638 of the outer zone 34 of light sources 38. Thus, power to the outer zone 34 of light sources 38 is increased to compensate for the loss of illuminance (power density) in the illumination pattern 52 of the beam of light 584 that would otherwise occur from spreading the light from the outer zone 34 of light sources 38. Increased power to the outer zone 34 of light sources 38 by itself however results in a second effect referred to as a "hot spot" in the center portion 642 of the beam of light 584, since in this illustrative embodiment the light emitted by the inner zone 14 of light sources 18 is not subject to beam spreading. Thus, the hot spot in the illustrative example may include for example a magnitude of illuminance at the center portion 642 being relatively higher than a magnitude of illuminance at the portion 640 surrounding the center portion 642. The control system 90 compensates for such hot spot effect by decreasing the total visible flux 618 from the inner zone 14 of light sources 18 and increasing the total visible flux 638 from the outer zone 34 of light sources 38 even further. The net effect is that the magnitude of the illuminance of the illumination pattern 52 is maintained substantially constant as the size of the illumination pattern 52 changes, and a substantially uniform illuminance is maintained across the illumination pattern 52 (i.e. minimization of the hot spot effect).

As described above, the illuminance of the illumination pattern 52 also naturally decreases radially outwardly from the center of the illustrative pattern 52 toward the perimeter of the illumination pattern 52. The control system 90 is configured to adjust power to the zones 14, 34 of light sources 18, 38 to maintain the decrease low, that is, where the d50/d10 ratio is greater than 0.5, and more preferably greater than 0.6. When the d50/d10 ratio is greater than 0.5, and more preferably greater than 0.6, the illuminance across the illumination pattern 52 may be said to be substantially uniform.

Thus, the control system 90 is configured to turn down the light output or total visible flux 618 from the inner zone 14 for the larger pattern size 84 shown in FIG. 3 relative to the light output or total visible flux 618 from the inner zone 14 for the smaller pattern size 74 shown in FIG. 2. The inventors have found that this prevents creating a noticeable "hot spot" in the center portion 642 of the relatively larger pattern size 84 from the beam of light 22 emitted by the inner zone 14 of light sources 18, which beam of light 22 is not spread but rather merely bent or redirected by the inner round housing lens 182. In addition, for the larger pattern size 84, the control system 90 is configured to increase the light output or total visible flux 638 from the outer zone 34 of light sources 38 so that the composite beam 584 formed by both the inner and outer zones 14, 34 of light sources 18, 38 has similar light density on the surface (illuminance) while also providing substantially uniform illuminance across the illumination pattern 52, that is, the illumination, or brightness, drops off smoothly from the center portion 642 of the beam to the edge.

Figure 8:
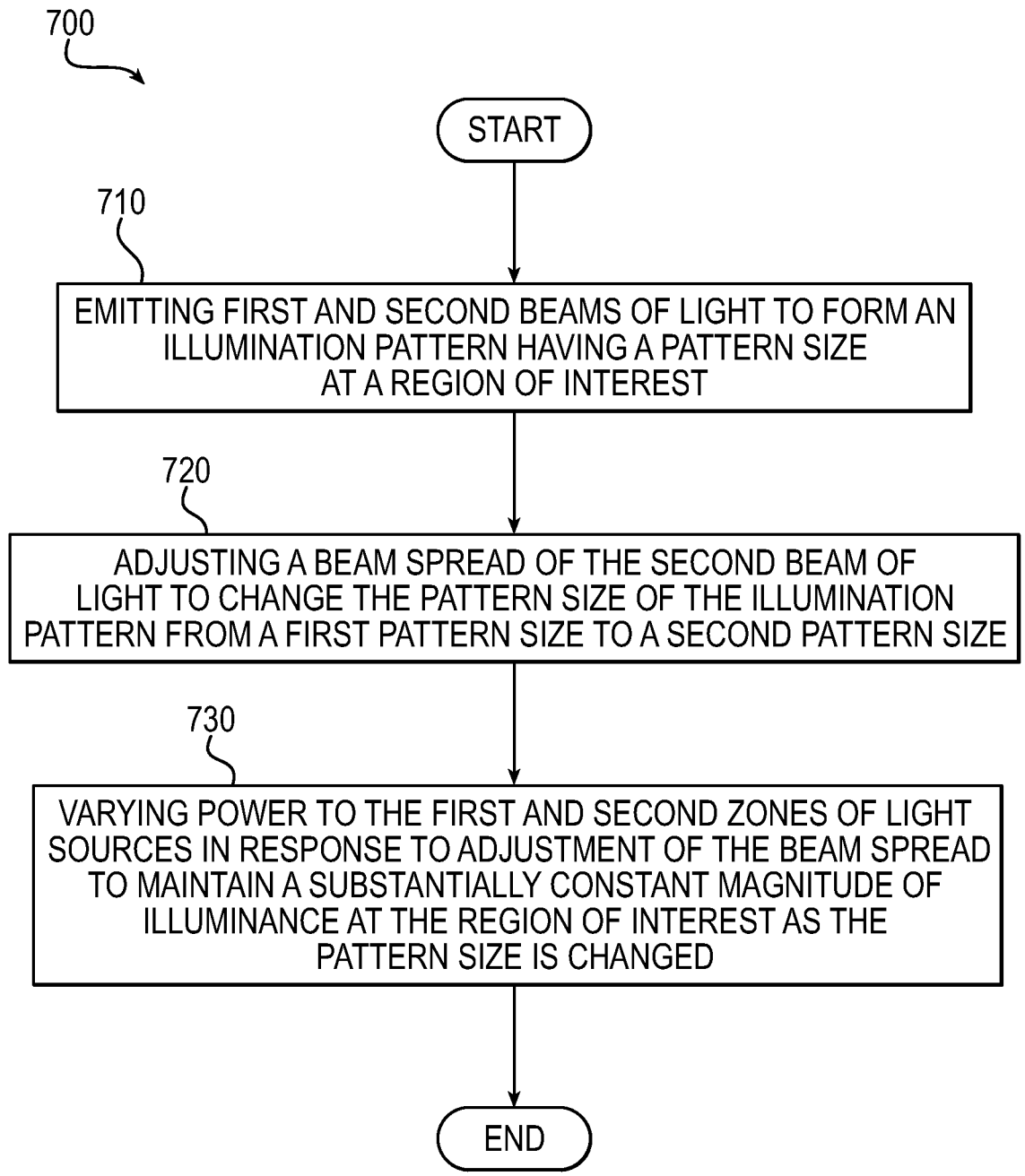
FIG. 8 shows a flowchart of a method in accordance with an embodiment of the invention.

Referring now to FIG. 8, there is shown a flowchart 700 of a method of operating a light head of a medical device support system, such as the afore described light head 12 of the medical device support system 10 of FIG. 1, in accordance with an embodiment of the invention. At step 710, first and second beams of light are emitted by respective first and second zones of light sources, for example the first and second zones 14, 34 of light sources 18, 38, wherein the first and second beams of light form an illumination pattern having a pattern size at a region of interest, such as the illumination pattern 52 at the region of interest 56. At step 720, a beam spread of the second beam of light is adjusted by an optical system, for example the optical system 60, in the path of the second beam of light to change the pattern size of the illumination pattern at the region of interest from a first pattern size to a second pattern size, for example the above described first and second pattern sizes 74, 84. At step 730, power to the first and second zones of light sources is varied for example by the control system 90, in response to adjustment of the beam spread of the second beam of light by the optical system to maintain a substantially constant magnitude of illuminance at the region of interest as the pattern size of the illumination pattern at the region of interest is changed from the first pattern size to the second pattern size.

Figure 9:
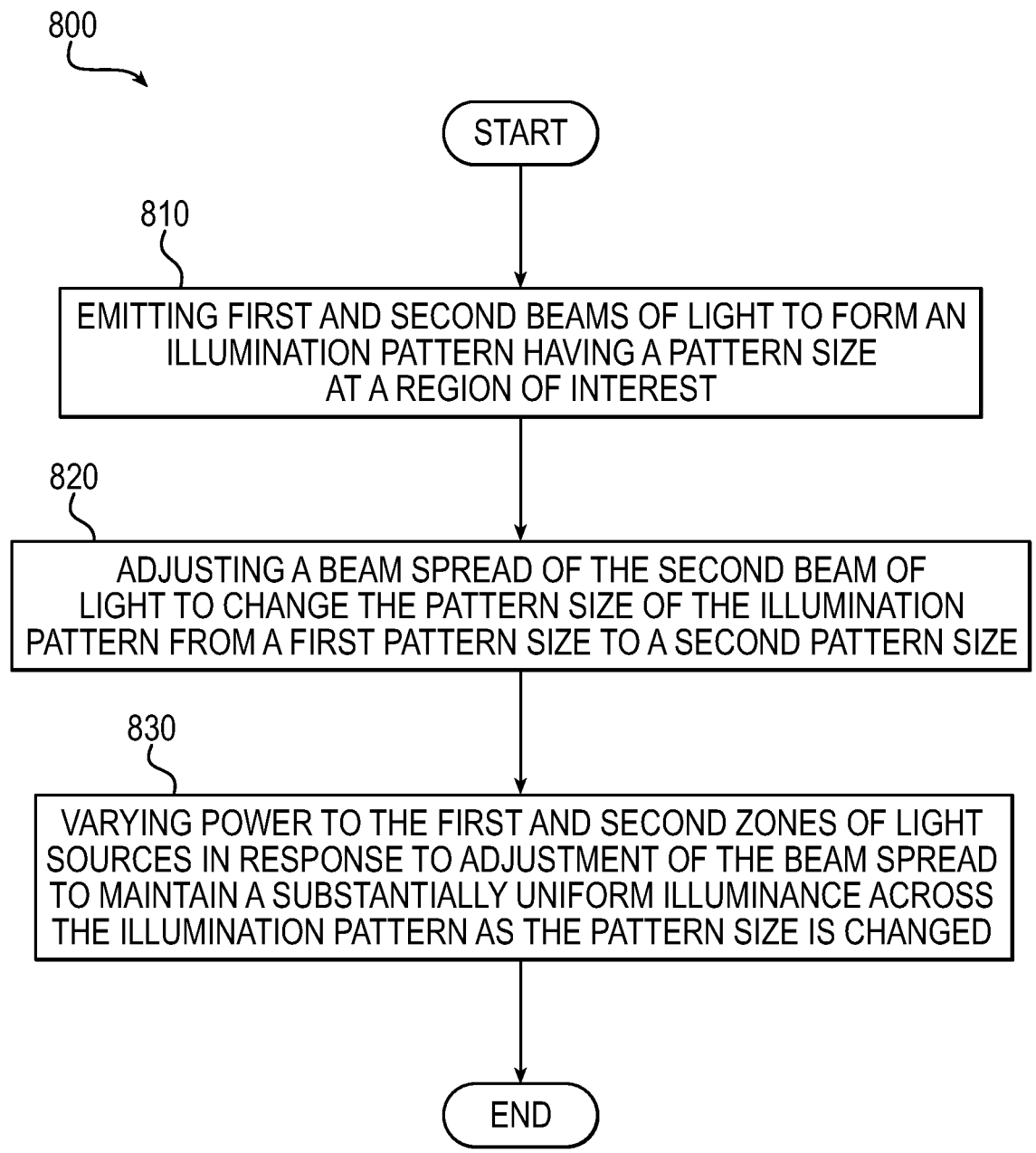
FIG. 9 shows a flowchart of a method in accordance with an embodiment of the invention.

Referring now to FIG. 9, there is shown a flowchart 800 of a method of operating a light head of a medical device support system, such as the afore described light head 12 of the medical device support system 10 of FIG. 1, in accordance with an embodiment of the invention. At step 810, first and second beams of light are emitted by respective first and second zones of light sources, for example the first and second zones 14, 34 of light sources 18, 38, wherein the first and second beams of light form an illumination pattern having a pattern size at a region of interest, such as the illumination pattern 52 at the region of interest 56. At step 820, a beam spread of the second beam of light is adjusted by an optical system, for example the optical system 60, in the path of the second beam of light to change the pattern size of the illumination pattern at the region of interest from a first pattern size to a second pattern size, for example the above described first and second pattern sizes 74, 84. At step 830, power to the first and second zones of light sources is varied for example by the control system 90, in response to adjustment of the beam spread of the second beam of light by the optical system to maintain a substantially uniform illuminance across the illumination pattern as the pattern size at the region of interest is changed from the first pattern size to the second pattern size.

The inventors have found the power balancing of the first and second zones 14, 34 of light sources 18, 38 to be advantageous over other systems. In other systems, when a relatively large pattern size is generated for example by beam spreading, the same amount of light is spread over the relatively larger area; thus, the total visible flux is constant, but the illuminance decreases due to the larger area of the pattern size. In contrast, in the present embodiment, as the pattern size increases for example from the FIG. 2 pattern size 74 to the FIG. 3 pattern size 84, the control system 90 varies the total visible flux 618, 638 of the light sources 18, 38, or power to the light sources 18, 38, so that the illuminance at the illumination pattern 52 is maintained substantially constant, whether at a certain portion of the illumination pattern 52 or an average of the illuminance at multiple portions of the illumination pattern 52. Thus, for example, the illuminance at the center of the illumination pattern 52 in FIG. 2 relative to the illuminance at the center of the illumination pattern 52 in FIG. 3 is maintained substantially constant. The control system 90 increases the light output (total visible flux) for the relatively larger pattern size 84, as represented by more rays of light being emitted from the light sources 38 in the second or outer zone 34 (from three rays in FIG. 2 to nine rays in FIG. 3), but produces substantially the same illuminance at the region of interest 56, depicted by the same density of the cross hatch patterns at the bottom of FIGS. 2 and 3, which represents the composite beam 584 formed by contributions from both the inner and outer zones 14, 34 of light sources 18, 38.

The inventors have also found that the beam spreading by the optical elements 170, 180 of the light head 12 is advantageous over other systems since the optical elements 170, 180 of the light head 12 provide a more consistent beam size, shape and uniformity with variations in distance from the light head 12 than the beams produced by the other systems where light is rigidly designed to form a desired beam at a specific distance. This is significant in many surgical lighting applications since surgical light heads typically are adjusted over a range of distances as the surgical team places the light head over a patient during a surgical procedure.

The inventors have also found that the light head 12 according to the present invention is advantageous over light heads for which some of the light sources are not used to produce a relatively smaller size pattern. The light head 12 according to the invention delivers light from a full diameter of the light head 12 when producing the relatively small pattern shown in FIG. 2, thus providing better shadow control.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A light head for a medical device support system, comprising:
   a first zone of light sources that emits a first beam of light and a second zone of light sources that emits a second beam of light, wherein the first and second beams of light form an illumination pattern having a pattern size at a region of interest;
   an optical system in a path of the second beam of light to adjust a beam spread of the second beam of light to change the pattern size of the illumination pattern at the region of interest from a first pattern size to a second pattern size; and,
   a control system configured to vary power to the first and second zones of light sources in response to adjustment of the beam spread of the second beam of light by the optical system to maintain a substantially constant magnitude of illuminance at the region of interest as the pattern size of the illumination pattern at the region of interest is changed from the first pattern size to the second pattern size.

2. The light head of claim 1, wherein the control system is configured to vary power to the first and second zones of light sources in response to adjustment of the beam spread of the second beam of light by the optical system to maintain a substantially constant magnitude of illuminance at a center of the region of interest as the pattern size of the illumination pattern at the region of interest is changed from the first pattern size to the second pattern size.

3. The light head of claim 1, wherein the control system is configured to increase power to the second zone of light sources and decrease power to the first zone of light sources in response to the second pattern size being adjusted to be relatively larger than the first pattern size.

4. The light head of claim 1, further comprising a handle mounted for rotational movement relative to a housing of the light head and coupled to the optical system, wherein rotation of the handle adjusts the optical system to adjust the beam spread of the second beam.

5. The light head of claim 4, wherein the optical system includes first and second wave lenses and rotation of the handle moves the first and second wave lenses relative to one another to adjust the beam spread of the second beam.

6. The light head of claim 4, wherein the control system is configured to detect rotation of the handle and vary the power to the first and second zones of light sources based on the detected rotation.

7. The light head of claim 1, wherein the illumination pattern includes a first illuminance at the first pattern size and a second illuminance at the second pattern size, where the second illuminance is no more or no less than 15 percent different (+/−15 percent) from the first illuminance.

8. The light head of claim 1, wherein the illumination pattern includes a first illuminance at the first pattern size and a second illuminance at the second pattern size, where the second illuminance is no more or no less than 10 percent different (+/−10 percent) from the first illuminance.

9. The light head of claim 1, wherein the illumination pattern includes a first illuminance at the first pattern size and a second illuminance at the second pattern size, where the second illuminance is no more or no less than five percent different (+/−5 percent) from the first illuminance.

10. The light head of claim 1, wherein the control system is configured to vary power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

11. The light head of claim 10, wherein the illumination pattern has a diameter and a center, wherein a d50/d10 ratio is defined as a ratio of the diameter at which the illuminance reaches 50 percent (50%) of the illuminance value at the center of the illumination pattern, referred to as d50, over the diameter at which the illuminance reaches 10 percent (10%) of the illuminance value at the center of the illumination pattern, referred to as d10, and wherein the substantially uniform illuminance across the illumination pattern includes the d50/d10 ratio being greater than 0.5.

12. The light head of claim 10, wherein the substantially uniform illuminance across the illumination pattern includes the d50/d10 ratio being greater than 0.6.

13. A light head for a medical device support system, comprising:
   a first zone of light sources that emits a first beam of light and a second zone of light sources that emits a second beam of light, wherein the first and second beams of light form an illumination pattern having a pattern size at a region of interest;
   an optical system in a path of the second beam of light to adjust a beam spread of the second beam of light to change the pattern size of the illumination pattern at the region of interest from a first pattern size to a second pattern size; and,
   a control system configured to vary power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

14. A method of operating a light head of a medical device support system, comprising:
- emitting first and second beams of light by respective first and second zones of light sources, wherein the first and second beams of light form an illumination pattern having a pattern size at a region of interest;
- adjusting a beam spread of the second beam of light by an optical system in the path of the second beam of light to change the pattern size of the illumination pattern at the region of interest from a first pattern size to a second pattern size; and,
- varying power to the first and second zones of light sources in response to adjustment of the beam spread of the second beam of light by the optical system to maintain a substantially constant magnitude of illuminance at the region of interest as the pattern size of the illumination pattern at the region of interest is changed from the first pattern size to the second pattern size.

15. The method of claim 14, wherein varying power includes varying power to the first and second zones of light sources in response to adjustment of the beam spread of the second beam of light by the optical system to maintain a substantially constant magnitude of illuminance at a center of the region of interest as the pattern size of the illumination pattern at the region of interest is changed from the first pattern size to the second pattern size.

16. The method of claim 14, further comprising varying power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

17. A method of operating a light head of a medical device support system, comprising:
- emitting first and second beams of light by respective first and second zones of light sources, wherein the first and second beams of light form an illumination pattern having a pattern size at a region of interest;
- adjusting a beam spread of the second beam of light by an optical system in the path of the second beam of light to change the pattern size of the illumination pattern at the region of interest from a first pattern size to a second pattern size; and,
- varying power to the first and second zones of light sources in response to adjustment of the beam spread of the second beam of light by the optical system to maintain a substantially uniform illuminance across the illumination pattern as the pattern size at the region of interest is changed from the first pattern size to the second pattern size.

* * * * *